(12) United States Patent
Gombert et al.

(10) Patent No.: US 9,901,411 B2
(45) Date of Patent: Feb. 27, 2018

(54) CONTROL DEVICE AND METHOD FOR CONTROLLING A ROBOT WITH A SYSTEM BY MEANS OF GESTURE CONTROL

(71) Applicant: ABB GOMTEC GMBH, Seefeld (DE)

(72) Inventors: Bernd Gombert, Worthsee (DE); Leopold Bock-Krausen, Munich (DE); Richard Roberts, Gilching (DE); Andras Acsai, Herrsching (DE)

(73) Assignee: ABB gomtec GmbH, Seefeld (DE)

( * ) Notice: Subject to any disclaimer, the term of this patent is extended or adjusted under 35 U.S.C. 154(b) by 0 days.

(21) Appl. No.: 15/025,899

(22) PCT Filed: Sep. 10, 2014

(86) PCT No.: PCT/EP2014/069284
§ 371 (c)(1),
(2) Date: Mar. 30, 2016

(87) PCT Pub. No.: WO2015/049095
PCT Pub. Date: Apr. 9, 2015

(65) Prior Publication Data
US 2016/0235489 A1 Aug. 18, 2016

(30) Foreign Application Priority Data

Oct. 1, 2013 (DE) .................. 10 2013 110 847

(51) Int. Cl.
*B25J 13/02* (2006.01)
*A61B 17/00* (2006.01)
(Continued)

(52) U.S. Cl.
CPC ............. *A61B 34/30* (2016.02); *A61B 34/37* (2016.02); *B25J 9/1689* (2013.01); *B25J 13/02* (2013.01);
(Continued)

(58) Field of Classification Search
CPC ... A61B 34/30; A61B 34/37; A61B 2034/302; A61B 2017/00207; A61B 2017/00017;
(Continued)

(56) References Cited

U.S. PATENT DOCUMENTS

2002/0082612 A1* 6/2002 Moll .................. A61B 19/2203
606/130
2003/0013949 A1* 1/2003 Moll .................. A61B 19/2203
600/407
(Continued)

FOREIGN PATENT DOCUMENTS

EP 2444006 A2 4/2012
EP 2614788 A1 7/2013
(Continued)

OTHER PUBLICATIONS

International Search Report in PCT/EP2014/069284 dated Nov. 17, 2014.
(Continued)

*Primary Examiner* — Jaime Figueroa
(74) *Attorney, Agent, or Firm* — Manelli Selter PLLC; Edward J. Stemberger

(57) ABSTRACT

The Invention relates to a control device (25, 28, 29) for controlling a robot system (11) with at least one robot arm (14, 18) on which a surgical instrument (15, 19) is secured that has an end effector (17, 21), wherein the control device (25, 28, 29) comprises an imaging system (25, 28) that records the control specification of at least one hand (30$_L$, 30$_R$), evaluates it and converts it to corresponding control commands for one or more components of the robot system (11). In order to simplify the control of the robot system (11) and in particular to make it intuitive, it is proposed that a control unit (25) be provided which determines the orientation and/or the position and/or the degree of opening of the end effector (15, 19) of a surgical instrument (15, 19) as first
(Continued)

parameter or first parameters, and moreover determines the orientation and/or the position and/or the degree of opening of at least one hand ($30_L$, $30_R$) as second parameter or second parameters, and, in the event of a deviation of one or more of the first parameters from the corresponding second parameter, suppresses a manual control of the end effector (17, 21), and, in the event of an agreement of one or more of the first parameters with the corresponding second parameter, frees a gesture control, such that the surgical instrument (15, 19) can be actuated by hand.

21 Claims, 6 Drawing Sheets

(51) Int. Cl.
  *A61B 34/30* (2016.01)
  *B25J 9/16* (2006.01)
  *A61B 34/37* (2016.01)
(52) U.S. Cl.
  CPC ............ *A61B 2017/00017* (2013.01); *A61B 2017/00207* (2013.01); *A61B 2017/00725* (2013.01); *A61B 2034/302* (2016.02); *G05B 2219/35444* (2013.01); *G05B 2219/36184* (2013.01); *G05B 2219/45123* (2013.01)
(58) Field of Classification Search
  CPC ............ A61B 2017/00725; B25J 13/02; B25J 9/1689; G05B 2219/45123; G05B 2219/36184; G05B 2219/35444
  USPC .................................................. 700/245, 259
  See application file for complete search history.

(56) References Cited

U.S. PATENT DOCUMENTS

| | | | |
|---|---|---|---|
| 2003/0216715 A1* | 11/2003 | Moll | A61B 19/2203 606/1 |
| 2005/0251110 A1* | 11/2005 | Nixon | B25J 9/1692 606/1 |
| 2008/0114494 A1* | 5/2008 | Nixon | B25J 9/1692 700/254 |
| 2011/0137322 A1* | 6/2011 | Moll | A61B 19/2203 606/130 |
| 2012/0083801 A1* | 4/2012 | Nixon | B25J 9/1692 606/130 |
| 2012/0130399 A1* | 5/2012 | Moll | A61B 19/2203 606/130 |
| 2013/0176220 A1* | 7/2013 | Merschon | G06F 3/017 345/158 |
| 2013/0274922 A1* | 10/2013 | Nixon | B25J 9/1692 700/254 |
| 2013/0304256 A1* | 11/2013 | Moll | A61B 19/2203 700/247 |
| 2014/0005484 A1* | 1/2014 | Charles | A61B 17/02 600/201 |
| 2014/0114481 A1* | 4/2014 | Ogawa | A61B 19/2203 700/257 |
| 2014/0195048 A1* | 7/2014 | Moll | A61B 19/2203 700/247 |
| 2014/0330434 A1* | 11/2014 | Nixon | B25J 9/1692 700/254 |

FOREIGN PATENT DOCUMENTS

| | | |
|---|---|---|
| JP | 2013510673 A | 3/2013 |
| WO | 2011060185 A1 | 5/2011 |
| WO | 2013005862 A1 | 1/2013 |

OTHER PUBLICATIONS

Office Action in DE 102013110847.4 dated Jun. 20, 2014.
Office Action in corresponding JP application No. Tokugan2016-519940 dated Oct. 27, 2017 and English translation thereof.

* cited by examiner

CONTROL DEVICE AND METHOD FOR CONTROLLING A ROBOT WITH A SYSTEM BY MEANS OF GESTURE CONTROL

The invention relates to a control device for controlling a robot system with at least one robot arm on which a surgical instrument having an end effector is secured, as well as a method for controlling such a robot system by means of gesture control.

Surgical interventions on human bodies are today carried out to an increasing extent with minimally invasive methods with the support of surgery robots. Depending on the type of intervention, the surgery robots can be equipped with various surgical instruments, such as, for example, endoscopes, cutting, gripping or sewing instruments. During an operation, the instruments are introduced into the body of the patient by means of one or more robots via a sheath. During the operation, the surgical instrument is then controlled by a surgeon via an input device of the robot system, such as, for example, an image processing system for gesture control.

A wide range of instruments are used for surgical use, such as, for example, endoscopes, laparoscopic instruments, cutting, gripping, holding, connecting or sewing instruments as well as other surgical tools. The actual end effector, such as, for example, a scalpel, scissors, a needle, a scraper, a file, a gripper, a camera etc., is located at the distal end of the surgical instruments or tools. The end effectors can, for example, be operated by means of a cable drive or with the aid of a manipulator integrated into the shaft of the instrument.

In a robot system having an input device for gesture control, the user can control the surgical instrument and the end effector thereof by manual control commands. The input device of the robot system comprises, in this case, a camera which detects the gestures executed by a user within a predetermined imaging region. The image data recorded by the camera is processed by an image processing unit (software) and is converted into corresponding control commands for the controlled components of the robot system. In the case of known gesture controls, the user can, as a rule, provide dynamic gestures such as, for example, movements, or static gestures such as, for example, hand signals, in order to control a specific component of the robot system. The controlled component is displayed to the user, as a rule, on a screen such that he can observe the reaction of the robot system to his control commands.

A robot system for minimally invasive surgery is known from U.S. Pat. No. 6,424,885 B1 which comprises several manual input devices with which the surgical instruments are controlled. In connection with the control, there is the problem that the orientation of the input device is to be brought into agreement with the orientation of an end effector of a surgical instrument. For this purpose, a method is applied in U.S. Pat. No. 6,424,885 A, which is referred to as "mapping". As is shown in FIG. 1, the input device 1 comprises two limbs 4, 5 which are secured to a base body 2 by a hinge and which can be pressed together or opened with the aid of a finger of a hand. During a manual actuation of the limbs 4, 5, the working elements 9, 10 of the controlled end effector 6, which is depicted on the right side, are moved accordingly. The position of the input device 1 is determined by a point $P_1$. The orientation of the input device 1 is determined by a longitudinal axis 3, which runs through the point $P_1$ and the base body 2 between the two limbs 4 and 5. Analogously to this, the orientation of the end effector 6 is set through an axis 8 running between the working elements 9 and 10. By means of the "mapping" method referred to above, the orientation of the input device 1 and the orientation of the end effector can be brought into agreement such that the two axes 3 and 8 run in the same direction.

The "mapping" method described in U.S. Pat. No. 6,424, 885 B1, however, is only suitable to align the orientation of an input device 1 with the orientation of an end effector. It is, however, not suitable to align the orientation, position and/or the degree of opening of a hand with that or those of an end effector.

It is therefore an object of the present invention to create a robot system having a device for gesture control in which a user can adapt the state of his hand simply and quickly to the state of the controlled object.

This object is solved according to the invention by the features specified in the independent claims. Further embodiments of the invention arise from the subordinate claims.

According to the invention, a control device for controlling a robot system is proposed which comprises an imaging system for gesture control which records the control command of at least one hand, evaluates it and converts it into corresponding control commands for one or more components of the robot system. The control device according to the invention comprises a control unit which determines the orientation and/or the position and/or the degree of opening of an end effector of a surgical instrument as a first parameter or first parameters, as well as the orientation and/or the position and/or the degree of opening of a hand as a second parameter or second parameters, and, in the event of a deviation of one or more of the first parameters from the respectively corresponding second parameter, suppresses the gesture control of the end effector, and, in the event of an agreement of at least one of the second parameters with the respectively corresponding first parameter or a target parameter dependent thereon, enables a gesture control of the end effector. According to the invention, it is therefore necessary to firstly adapt the orientation, the position or the degree of opening of the hand to the orientation, the position and/or the degree of opening of the instrument to be controlled or the end effector thereof—so to implement an alignment. After such an alignment, the surgical instrument or the end effector thereof can then be manually controlled.

The activation of the gesture control can occur automatically. It can, however, also be switched to active if an additional condition is fulfilled, such as, for example, that the user operates the gesture control again. In this case, the gesture control would then only be possible if an alignment between the hand and the end effector as well as an additional actuation by the user has taken place.

According to a preferred embodiment of the invention, the device for gesture control is configured in such a way that at least two of the states: orientation, position and degree of opening of the controlling hand, must agree with the corresponding state of the end effector in order to activate the gesture control.

In order to request the user to implement an alignment, the control device according to the invention is preferably designed in such a way that, in the event of a deviation of at least one of the hand states from the corresponding state of the end effector, a signal is output to the user. This signal can, for example, be an optical, aural or haptic signal. With the signal, the user is requested to adapt the orientation and/or position and/or the degree of opening of the hand to the corresponding state of the end effector.

In the event of an agreement of at least one of the states, a signal is preferably emitted to the user which displays the successful alignment to the user. Therefore, for example, the successful alignment can be indicated to the user by means of an optical signal.

In order to facilitate the alignment between the hand and the end effector, for example, a virtual element can be overlaid on a screen, the orientation and/or position and/or degree of opening thereof corresponds to that or those of the hand. The virtual element can, for example, be a reproduction of the controlled end effector. In the case of scissors, for example, the image of surgical scissors can be depicted, or in the case of a scalpel, the image of a scalpel.

Additionally, a further reference element can be displayed which depicts the orientation and/or position and/or the degree of opening of the controlled end effector and which serves, to the user, as a target specification for the alignment between the hand and the end effector. The user can therefore simply and intuitively adapt the orientation and/or position and/or the degree of opening of the hand to the target specification of the reference element. He can thereby follow the alignment process on the screen.

To determine the orientation, the position or the degree of opening of a hand, there is, in principle, several possibilities. According to one embodiment of the invention, the position of a hand can be determined, for example, by a characteristic point being recognised on the hand or the associated arm by the imaging system and this point being set as a reference point for the position of the hand. The imaging system can, for example, determine a wrist joint point, a point on the fingertip or a point on a knuckle as a reference point. The position of this point is determined by the control unit, preferably in the coordinate system of the imaging system.

The orientation of the hand can, for example, be set by a vector, the direction of which is determined in the coordinate system of the imaging system. The vector can, for example, lie on a line between the wrist joint and the fingertip of the index finger, or between the wrist joint and the tip of the thumb. It could, for example, however, also lie on a line which runs between the thumb and the index finger in the direction of the wrist joint. In principle, any vectors can be determined which are then set as a reference for the orientation of the hand. The recognition of the orientation vector or of the associated line preferably occurs automatically by the imaging system. The orientation of the hand is preferably determined in the coordinate system of the imaging system.

The degree of opening of the hand can, for example, be determined by two vectors being set and the angle between the vectors in the coordinate system of the imaging system being determined. A first vector can, for example, point from a point on the wrist joint in the direction of the thumb, and a second vector from the point on the wrist joint in the direction of the tip of the index finger. The vectors or the associated lines can be determined automatically by the imaging system.

The control device for the robot system according to the invention can furthermore comprise a manually operated auxiliary element which serves to guide the hand movement of the user. According to a preferred embodiment of the invention, the auxiliary element has the same number of degrees of freedom of movement as the controlled end effector of the surgical instrument. In the case of a gripper in which two gripping jaws arranged opposite each other can move towards or away from each other around an axis, the auxiliary element preferably has precisely one degree of freedom. It can, however, also have more or fewer degrees of freedom.

The shape of the manually operated auxiliary element preferably corresponds to the shape of the controlled end effector. In the case of surgical scissors or a gripper, the auxiliary element can, for example, have two limbs which are connected to each other via a joint and can therefore be moved back and forth.

According to one embodiment of the invention, for example, the orientation, the position and/or the degree of opening of the auxiliary element can be detected by the imaging system. The thus obtained pieces of information can then be used as reference parameters for the orientation, position and/or the degree of opening of the hand. As the manually operated auxiliary element has clearly defined elements, the orientation, the position and/or the degree of opening of the auxiliary element and therefore also the hand can be determined particularly simply and precisely. This method therefore offers advantages of a detection of points on the hand. If necessary, markings can also be provided on the auxiliary element in order to further simplify the recognition.

According to the invention, using the control, as many points on the hand or the auxiliary element can be specified as are necessary for the determination of the orientation, the position and the degree of opening of the hands. If auxiliary elements are used for the gesture control, then points can also be set on the auxiliary elements. For example, further points can be determined which lie on the fingertips or the limb ends of the auxiliary elements.

These points can then also be used to set a vector. For example, the vector can be defined such that it must run through two points. Alternatively, three points on a hand and/or on the auxiliary element can be used in order to span a virtual plane on which the vector must lie.

Furthermore, the points located on the tips or on the limb ends of the auxiliary element can be used in order to determine the degree of opening of the hands by the distance between the fingertips being determined. The greater the distance between two points, the greater the degree of opening of the finger.

Alternatively or additionally, the manually operated means can also comprise a sensor, in particular an inertial sensor which, for example, can measure the position in space and/or a movement in or around three spatial axes. The sensor data can, for example, be transferred in a contactless manner to a control unit. The data supplied by the sensor can, in turn, be used to determine the orientation, position and/or the degree of opening of the hand.

According to a preferred embodiment of the invention, the orientation, the position and/or the degree of opening of the hand are determined redundantly by at least two of the methods referred to above, i.e. by optical recognition of the hand, optical recognition of the auxiliary element and/or with the aid of a sensor integrated into the auxiliary element. The susceptibility to errors of the gesture control can thereby be clearly reduced and the reliability of the system improved.

A control command of the hand is preferably converted into a corresponding movement of the end effector using a predetermined scaling factor. In the case of a scaling factor of one, the end effector is moved with the same scale as the hand. The scaling factor can, however, also be adjusted to be larger or smaller. Therefore, for example, a hand movement can cause a movement of the end effector which has been reduced by a factor of 2; i.e. that a reduction of the degree of opening of the finger by 20° would cause a reduction of the angle of opening of the working limb by 10°. Different scaling factors can also be defined for different types of movement or degrees of freedom. For example, for each movement along and/or around the axes x,y,z, a separate scaling factor could be selected for the hand movements as well as for the ratio of the angle of opening and the degree of opening. Different scaling factors can also be defined respectively with regard to the conversion of the distance, the speed and the acceleration. The scaling factors are therefore able to be adjusted in any manner according to the invention. They can therefore also vary depending on the location at which the end effector is located.

As was referred to at the beginning, the gesture control comprises an imaging system which records and evaluates the manual gestures executed by the user. The control of the surgical instrument or of the end effector is preferably active as long as the controlling hand is located within a predetermined imaging region. If the hand leaves the imaging region, the control is preferably deactivated.

The control device according to the invention also comprises a camera which records the controlled object and a screen on which the recorded image is depicted. According to a preferred embodiment of the invention, the controlled object is depicted on the screen, such that the movement of the object on the screen agrees with the corresponding movement of the hand. The object imaged on the screen is therefore moved in relation to a coordinate system of the screen display in the same direction as the movement of the hand in relation to the coordinate system of the imaging system. If the user moves his hand, for example, upwards (in the z-direction of the coordinate system of the imaging system), then the image of the end effector depicted on the screen is likewise moved upwards (in the z-direction of the coordinate system of the screen display). The real movement of the end effector, however, runs, as a rule, in another direction. The movement of the end effect, however, is depicted in the same direction as the movement of the hand on the screen. Such a depiction has the fundamental advantage that a user, such as, for example, a surgeon, can very simply and intuitively control the robot system. Therefore, no long training time or even rethinking is required.

In order to implement this type of depiction, a coordinate system is allocated to the camera which records the end effector, said coordinate system being aligned to the image axes of the image recorded by the camera. The coordinate system of the camera has, as a rule, a different orientation from the coordinate system of the imaging system. With regard to the camera, however, it preferably has the same orientation as the coordinate system of the imaging system with regard to the detection region or the coordinate system of the screen display with regard to the screen.

In the case of a hand movement within the imaging region, the end effector is preferably controlled in such a way that it moves in the same direction in the coordinate system of the camera as in the coordinate system of the imaging system. If the user, for example, implements a movement in the z-direction in the coordinate system of the imaging system, the end effector likewise moves in the z-direction, but in the coordinate system of the camera. The z-coordinate of the camera is, in turn, depicted as a z-coordinate in the coordinate system of the screen. The same also applies analogously to the other coordinates. The control unit according to the invention is therefore designed such that a control command of a hand in the coordinate system of the imaging system is converted into a corresponding action of the end effector in the coordinate system of the camera.

The orientation, the position and/or the degree of opening of the end effector are known parameters, since the robot system usually has a plurality of sensors with which the parameters referred to can be measured. Therefore the information present in the system can be used to recognise the orientation, the position and/or the degree of opening of the end effector. Since the control unit generates the control commands for the end effector, the parameters referred to are therefore also known to the control unit.

Additionally, all coordinate systems are known to the control unit such that a parameter from one coordinate system can be converted into a corresponding parameter of the other coordinate system by means of a coordinate transformation. Therefore, the end effectors can always be operated in the camera coordinate system, independently of how the camera coordinate system is aligned to another coordinate system.

Alternatively, the orientation, position and/or the degree of opening of the end effector could, however, also be obtained from the image data recorded by a camera, analogously to the imaging of the hand or of the auxiliary element.

The invention also relates to a method for controlling a robot system by means of gesture control. According to the invention, the orientation and/or the position and/or the degree of opening of an end effector of a surgical instrument are determined as a first parameter or as first parameters and the orientation and/or the position and/or the degree of opening of at least one hand are determined as a second parameter or second parameters. In the event of a deviation of one or more of the first parameters from the respectively corresponding second parameter, a manual control of the end effector is automatically suppressed. As soon as one or more of the corresponding parameters agree, the gesture control is preferably automatically enabled. In the latter case, the alignment between the hand and the controlled end effector was successful—i.e. the orientation, the position and/or the degree of opening of the hand and the end effector agree. After the alignment, the end effector can be controlled by gesture control. It can, however, also be provided that the user must operate the gesture control again in order to activate it completely.

BRIEF DESCRIPTION OF THE DRAWINGS

The invention is explained in more detail below by means of the enclosed drawings. Here are shown.

Figure 1:
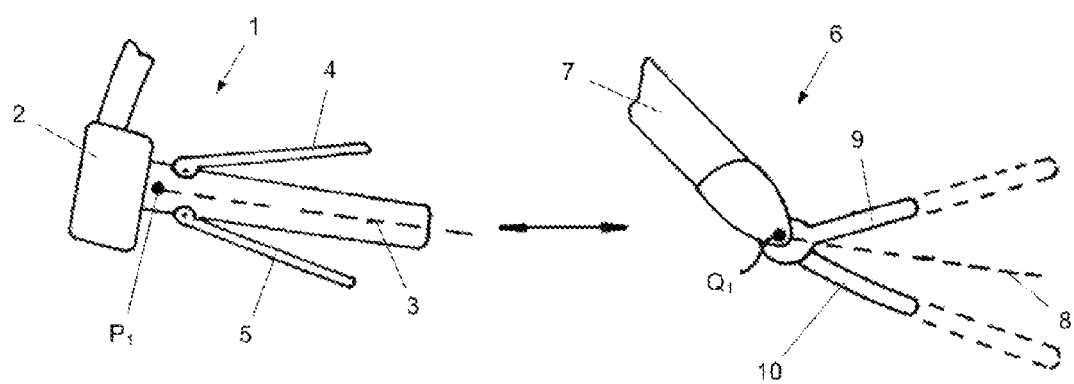
FIG. 1 a depiction of an input device known from prior art and an end effector controlled therewith.

With regard to the explanation of FIG. 1, reference is made to the introduction of the description.

Figure 2:
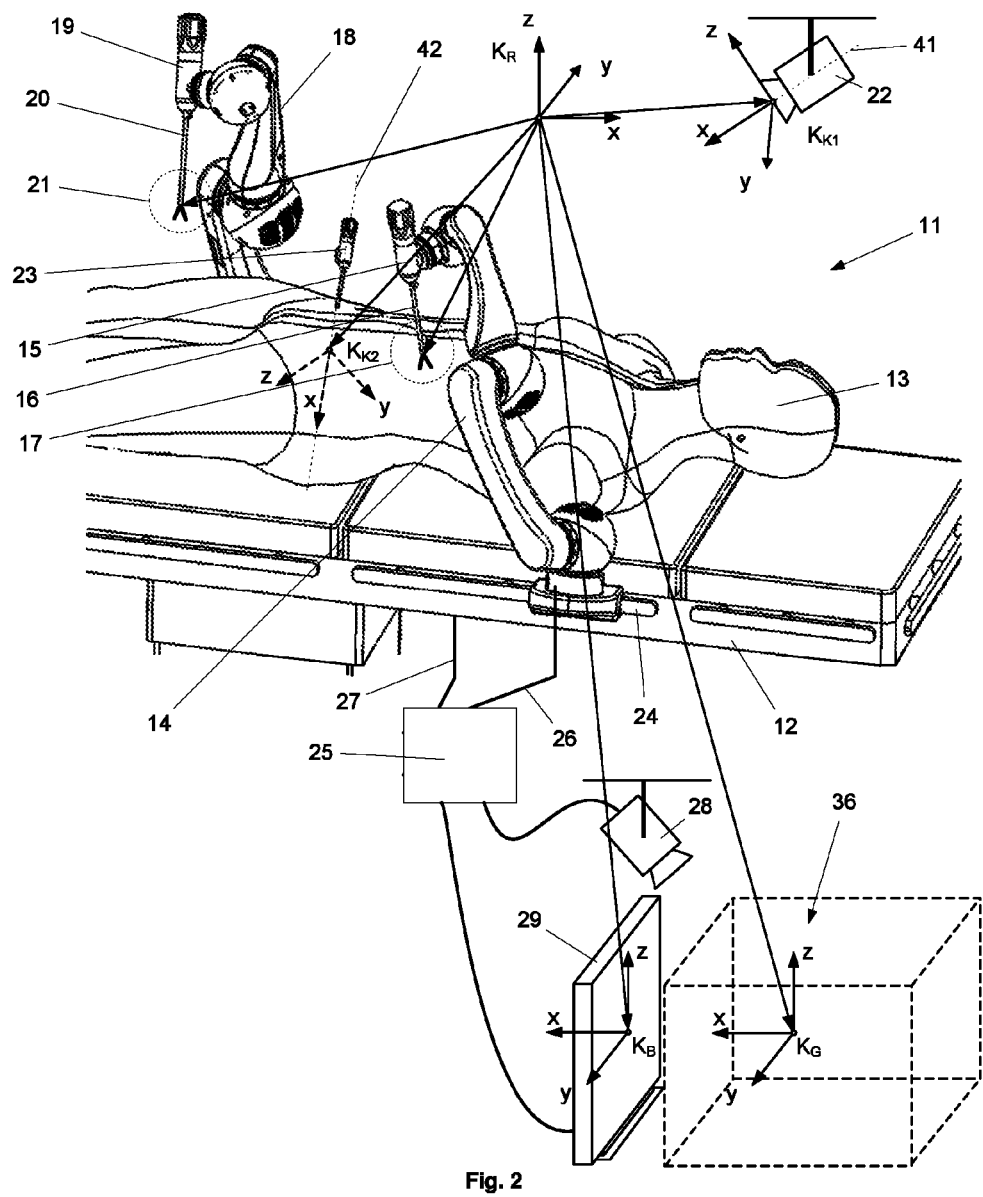
FIG. 2 a perspective view of a robot system for minimally invasive surgery having two robot arms and a control device to implement a gesture control.

FIG. 2 shows a schematic depiction of a robot system 11 for minimally invasive surgery having two robot arms 14, 18 and a control device for controlling the different components of the robot system 11 by means of gesture control. The robot arms 14, 18 are secured here to an OP table 12 via a rail 24. The robot arms 14, 18 can thereby be constructed in the same manner or differently. A patient 13 lies on the OP table 12, on whom a surgical intervention is to be carried out.

The robot arms 14 and 18 are each equipped with a surgical instrument 15 or 19. Surgical instruments can in principle be all instruments which are suitable for a surgical intervention, such as, for example, a scalpel, a gripper, scissors, electro-surgical instruments, endoscopes, a camera, staple, etc. The instrument 15 can, for example, be formed as scissors, and the instrument 19 as a gripper. The instruments 15, 19 typically have a shaft 16, 20 on the distal end of which an end effector 17, 21 corresponding to the function of the instrument is attached (see FIG. 3).

The instruments 15, 19 are moved by the robot arms 14 and 18 and introduced into the body of the patient 13 via small artificial openings. The actual surgical intervention can then be implemented by operation of the end effectors 17 or 21.

To control the end effectors 17, 21—this is understood below to be the positioning and orientation in space as well as the actuation of the actual working elements—a control device is provided with an image processing system. The imaging system comprises a camera 28 which monitors a cubic detection region 36. The imaging system is thereby able to recognise and interpret manually executed gestures. The image data recorded by the camera is transmitted to a control unit 25 and evaluated by an evaluation unit (software) contained therein. The control unit 25 then generates control commands corresponding to the recognised gestures, with which control commands the actuators of the controlled components 14, 15, 17, 18, 19, 21 are controlled. The robot arms 14, 18, the instruments 15, 19 and/or the end effectors 17, 21 can thereby each be operated individually or all at the same time.

According to one exemplary embodiment, for example, the left end effector 21 can be operated with the left hand $30_L$ of the user and the right end effector 17 with the right hand $30_R$. By the term "operation" of the end effector, it is here understood that the end effector 17, 21 can be positioned or orientated in three-dimensional space and a certain function, such as, for example, cutting, gripping or coagulating, can be executed. The end effectors 17, 21 can optionally be controlled or regulated in terms of position and/or speed.

The robot arms 14 and 18 are connected here to the control unit 25 via a respective cable 26 or 27. Alternatively, a wireless control could also be provided.

As has been explained above, a predetermined detection region 36 is available to the user in which he can execute manual gestures in order to control the robot system 11. The control device is preferably designed such that only gestures which are executed within this region 36 are converted into corresponding control commands by the control unit 25. Gestures implemented outside the detection region 36 are, however, not converted into corresponding control commands.

The detection region 36 has a first coordinate system $K_G$ in which the positions of the hands $30_L$, $30_R$ as well as the orientation thereof in three-dimensional space are able to be determined clearly. Therefore, for example, the direction can be determined in which the hand $30_L$, $30_R$ or the fingers thereof are pointing, as well as the distances of the hands $30_L$, $30_R$ or fingers to each other. Additionally, the movement of the hands $30_L$, $30_R$ or the fingers thereof can be determined, such as, for example, the distance covered, the movement speed and/or the movement direction.

Figure 4:
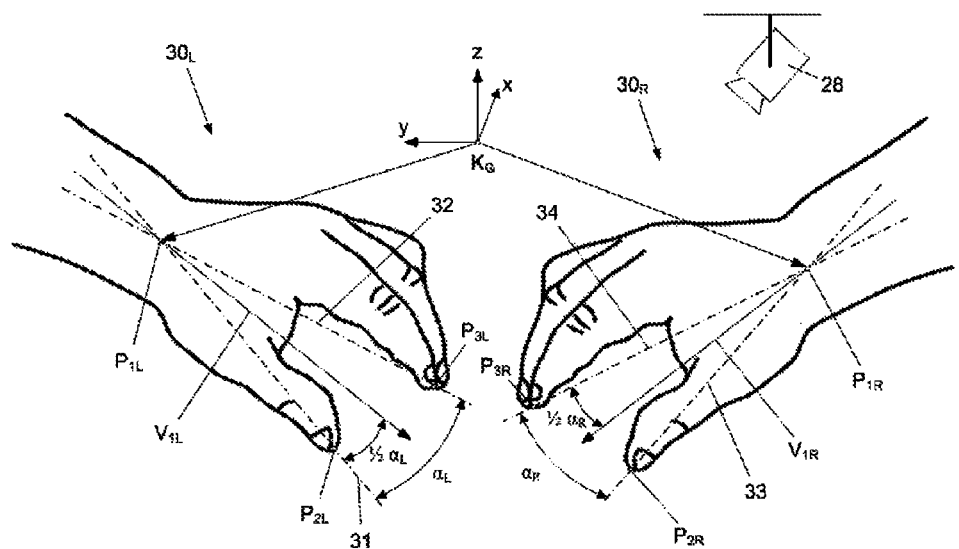
FIG. 4 a depiction of two hands and different reference points and lines to determine the orientation, the position and the angle of opening of the hands.

In order to determine the position of a hand $30_L$, $30_R$, one or more points on the hand $30_L$, $30_R$ and/or the associated arm can be recognised with the aid of the imaging system and can be used as a reference point for the position of the respective hand $30_L$, $30_R$. As is shown in FIG. 4, for example, the points $P_{1L}$ of the left hand $30_L$ and $P_{1R}$ of the right hand $30_R$ are determined, which lie on the wrist joint of the hands $30_L$, $30_R$ respectively. The position of the two hands $30_L$, $30_R$ can therefore be described clearly in the coordinate system $K_G$.

Additionally, further points on the hands, such as, for example, the points $P_{2L}$, $P_{2R}$ and $P_{3L}$, $P_{3R}$ on the fingertips of the thumb and index finger of the left and right hand $30_L$, $30_R$ can also be defined as reference points. In order to determine the orientation of the hands $30_L$, $30_R$, a respective line 31, 32, 33 or 34 can be laid between two points of the hand $30_L$ or $30_R$. The orientation of a hand $30_L$, $30_R$ can, for example, be defined as a vector which lies on one of the lines 31 to 34 referred to. Alternatively, however, a vector $V_{1L}$, $V_{1R}$ could also be defined which lies between the lines 31 and 32 or 33 and 34 referred to. Such a vector could lie in a plane which is spanned by the points $P_{1L}$, $P_{2L}$ and $P_{3L}$ of the left hand $30_L$ or by the three points $P_{1L}$, $P_{2R}$ and $P_{3R}$, of the right hand $30_R$. This vector $V_{1L}$, $V_{1R}$ is then used as a reference for the orientation of the hand $30_L$ or $30_R$.

Alternatively, the vectors $V_{1L}$ and $V_{1R}$ could, however, also enclose any other angle and, for example, point directly to the fingertip of the index finger (point $P_{3L}$ or $P_{3R}$).

The degree of opening of a hand $30_L$, $30_R$ between the thumb and the index finger can, for example, be defined by the angle $\alpha_L$ or $\alpha_R$ between the lines 31 and 32 or 33 and 34. This angle $\alpha_R$, $\alpha_L$ is dependent on the distance between the thumb and the index finger. The degree of opening of a hand $30_L$, $30_R$ can, however, also be determined by the distance of two points $P_{2L}$, $P_{2R}$, $P_{3L}$, $P_{3R}$ on the hand $30_L$, $30_R$, for example by the distance of the tip of the index finger $P_{3L}$ and the tip of the thumb $P_{2L}$.

The position, orientation and the degree of opening of a hand $30_L$, $30_R$ are therefore able to be determined clearly in the coordinate system $K_G$. Additionally, an associated speed or acceleration can be determined for any change of position, orientation and degree of opening.

As shown in FIG. 4, the vectors $V_{1L}$ or $V_{1R}$ advantageously always enclose half of the angle of opening $\alpha_L$ or $\alpha_R$ between the lines 31 and 32 or 33 and 34.

Figure 5:
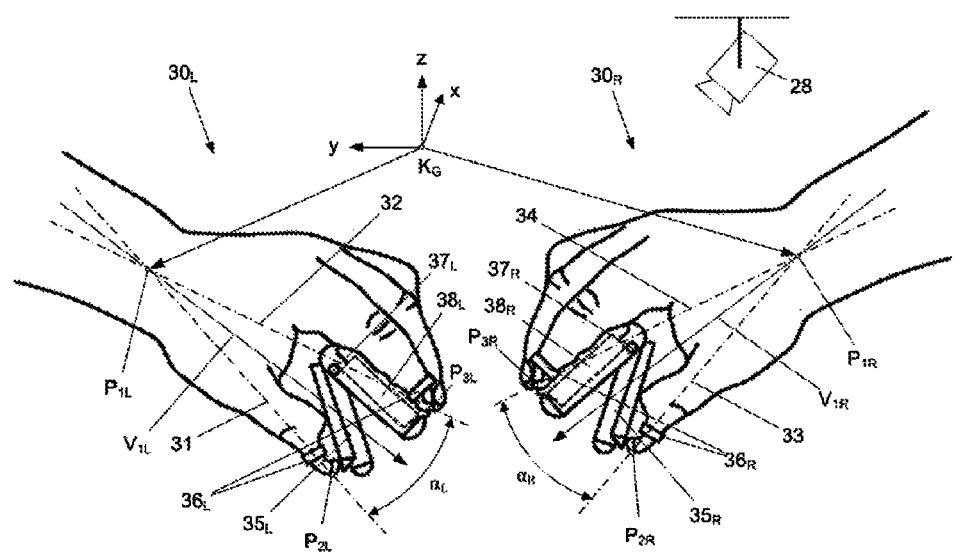
FIG. 5 a depiction of two hands similar to FIG. 4, wherein each hand holds an auxiliary element to guide the hand movements.

Besides the recognition described above of hand or arm points, there are, however, yet further different possibilities to determine the position, the orientation or the degree of opening of a hand. As is shown in FIG. 5, the control device of the robot system 11 can also comprise manually operated auxiliary elements $35_L$, $35_R$ which serve to guide an opening and closing movement of the hand between thumb and index finger. In the depicted exemplary embodiment, an individual guide element $35_L$, $35_R$ is provided for each hand $30_L$, $30_R$.

Each auxiliary element $35_L$, $35_R$ comprises two limbs which are connected to each other by a hinge and which correspond in their shape and arrangement to a gripper or surgical scissors. The auxiliary elements $35_L$, $35_R$ each have precisely one degree of freedom, i.e. only movement towards or away from each other of the thumb tip and index fingertip around a defined axis 37 is possible. Due to this limitation of the freedom of movement of thumb and index finger, incorrect interpretations can therefore be excluded during gesture recognition, as the fingertips can only move along a fixedly defined path. The moving limbs of the auxiliary elements $35_L$, $35_R$ can, for example, have loops $36_L$, $36_R$ into which the user can insert his thumb or index finger.

In an analogous manner, for the determination of distinctive points on the hands $30_L$, $30_R$, points can also be determined on the auxiliary elements $35_L$, $35_R$ and from this the position, orientation and/or the degree of opening of the associated hand $30_L$ or $30_R$ can be determined. Instead of the wrist joint points $P_{1L}$ or $P_{1R}$, for example, the joint points $37_L$ or $37_R$ of the auxiliary element could be used which are depicted in FIG. 5. Instead of the vectors $V_{1L}$ and $V_{1R}$, for example, the joint axes could be used, which run through the points $37_L$ or $37_R$. The angle between the limbs of an auxiliary element $35_L$ or $35_R$ which are connected to each other by a hinge or the distance between the two limb ends (analogously to the fingertips), for example, could be used as a reference for the degree of opening of the hand.

Alternatively or additionally, the auxiliary elements $35_L$ and $35_R$ could each be equipped with a sensor system $38_L$ and $38_R$. This sensor system can likewise be used to determine the position, the orientation and/or the degree of opening of the hand. If, for example, an angle sensor is provided which measures the angle of the two limbs which are connected to each other by a hinge, the degree of opening of the hand $30_L$ or $30_R$ between the thumb and index finger can be determined. Additionally, magnetic sensors, acceleration or inertial sensors could also be integrated, with which the position, the orientation, but also a movement speed or acceleration of the hand $30_L$ or $30_R$ can be detected. The sensor data can, for example, be transferred in a contactless manner to the control unit 25. Redundant pieces of information can be compared to one another in order to detect or rectify possible errors. A missing or incorrect piece of information can, for example, also be replaced by a piece of information which is present in a redundant manner.

Figure 3:
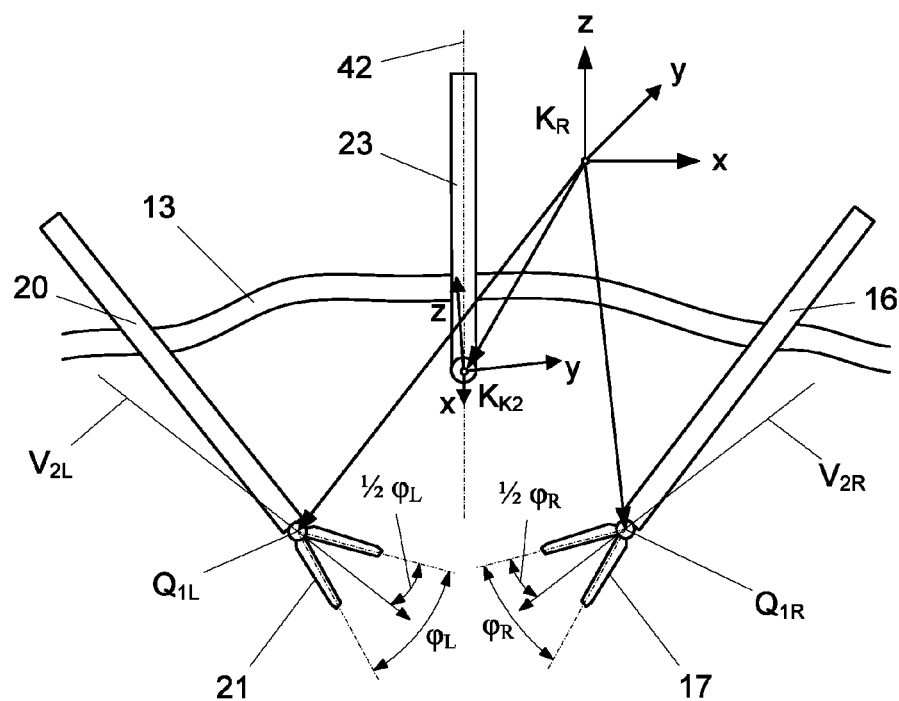
FIG. 3 a side view of several surgical instruments which are introduced into the body of a patient.

During a minimally invasive operation, the location at which the intervention takes place is monitored by one or more cameras 22, 23. For this purpose, one or more laparoscopic instruments are introduced into the body of the patient 13 through small artificial openings, as is also depicted in FIG. 3. The image of the camera 23 is depicted on a screen 29 on which the surgeon can observe and monitor the progress of the operation. Additionally, a further camera 22 is provided in the robot system 11 of FIG. 2, said camera recording the events outside the body of the patient 13. This camera 22 can, for example, be used to detect the position and orientation of the robot arms 14, 18 as well as the instruments 15 and 19 and the camera 23. The image of camera 22 and the camera 28 can also be depicted on the screen 29. It can also be switched back and forth between the cameras 22 and 23 automatically or manually depending on whether an end effector is located within or outside the patient. Optionally, the image on the screen 29 can be shared in order to display an end effector detected by the camera 22 and an end effector detected by the camera 23.

Preferably, all cameras and/or screens are 3D-capable. Devices known from prior art can be used for this purpose, for example stereoscopic cameras or cameras having dual image recording. In order to enable a control of the surgical instruments 15, 19, including their end effectors 17, 21, which is as intuitive as possible for the surgeon, at least the orientation, but preferably also the position and the degree of opening of the controlling hand $30_L$ or $30_R$ in relation to the coordinate system $K_G$ should agree with the orientation, the position or the degree of opening of the controlled end effector 17 or 21 in relation to the respective camera coordinate system $K_{K1}$ or $K_{K2}$. In the case of the robot system 11 depicted here, for this purpose, an alignment process is implemented in which the user can adapt the orientation and/or the position and/or the degree of opening of his hand to the corresponding state of the controlled end effector 17 or 21.

As soon as an agreement of at least one of the state parameters referred to, preferably all state parameters, has been achieved, the controlled end effector 17, 21 is enabled or activated and can then be controlled by hand. The activation can occur automatically or require an additional operation of the user.

In order to simplify the alignment between his hands $30_L$, $30_R$ and the controlled end effector 17, 21 for the user, in this exemplary embodiment, a virtual end effector 17' is overlaid on the screen 29, the orientation, position and degree of opening of which corresponds to the orientation, position and the degree of opening of the controlling hand, for example $30_R$. The virtual end effector 17' therefore represents the state of the controlling hand, for example $30_R$. Additionally, a further end effector 17" is imaged in the window 40, said further end effector depicting the state of the controlled end effector 17. The first virtual end effector 17' therefore displays an actual state of his hand $30_R$ to the user and the further end effector 17" the target state of the hand $30_R$.

Figure 6:
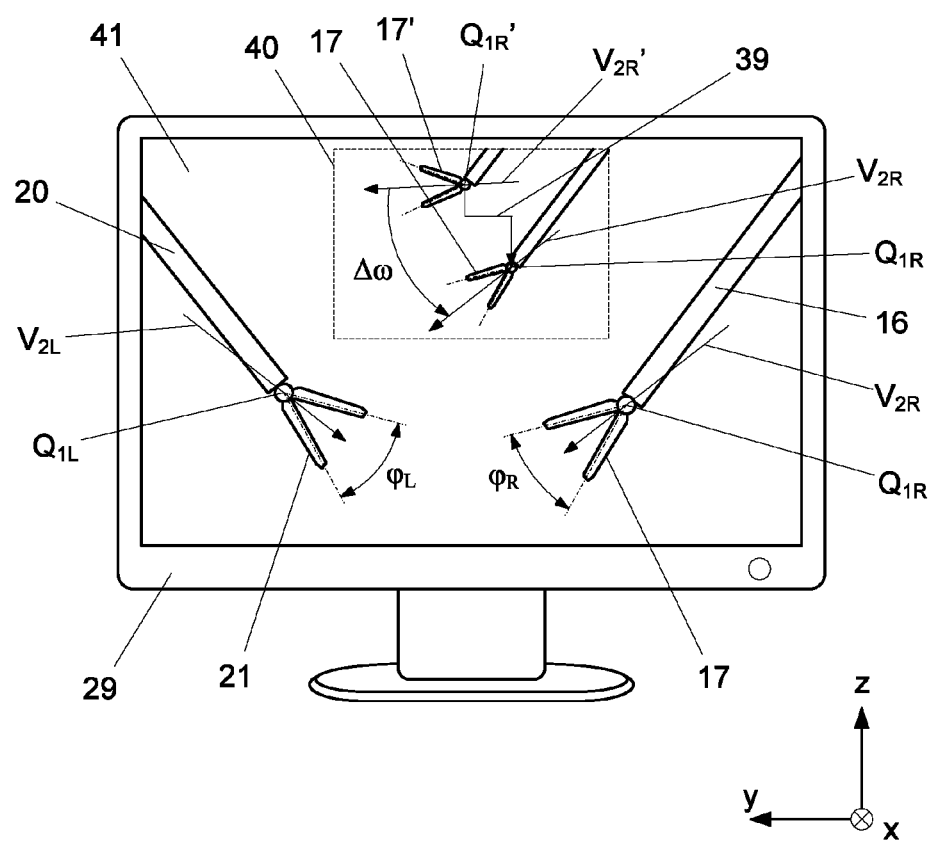
FIG. 6 a screen on which the end effectors controlled by means of gesture control as well as two virtual end effectors are depicted.

As is shown in FIG. 6, the orientation of the hand $30_R$ and the orientation of the end effector 17 differ by an angle $\Delta\omega$. In order to bring the orientation of the right hand $30_R$ into agreement with the orientation of the end effector 17, the user only has to change the orientation of his hand. The robot system 11 can also additionally display to the user how he must move his hand, for example by overlaying of arrows. If the orientation of the hand $30_R$ agrees with the orientation of the end effector 17, feedback to the user can likewise occur such as, for example, by displaying a symbol on the screen 29 or by coloured highlighting of the virtual end effector 17'. Depending on the design of the robot system 11, tolerances can be specified for the agreement of the orientation. An exact agreement is not necessarily required.

In an analogous way, the orientation of the left hand $30_L$ can also be brought into agreement with the left end effector 21. After the alignment of the orientation, the gesture control of the two end effectors 17, 21 is enabled. Additionally, the window 40 can be hidden. As a requirement for an activation of the gesture control, it can be provided that, besides the orientation, one or more further states of the hand $30_R$, $30_L$, must be brought into agreement with the respectively controlled end effector 17, 21. Therefore, for example, it can be provided that the degree of opening $\alpha_L$ and $\alpha_R$ of the two hands $30_L$ and $30_R$ must be brought into agreement with the angles of opening $\phi_L$ and $\phi_R$ of the two end effectors 17, 21. The alignment of the degree of opening can occur analogously to the alignment of the orientation, as has been described above. Therefore it is determined whether the degree of opening of a hand $30_L$, $30_R$ deviates from the degree of opening of the controlled end effector 17, 21. In the event of a deviation, the user can in turn be required to change the degree of opening $\alpha_L$, $\alpha_R$ of his hand $30_L$, $30_R$. After the adaptation has occurred, the gesture control can in turn be automatically enabled. During the alignment, an offset can be defined between the degrees of opening $\alpha_L$ and $\alpha_R$ of the two hands $30_L$ and $30_R$ and the angles of opening $\phi_L$ and $\phi_R$ of the two end effectors 17, 21. This offset can, for example, cause the fingers to not have to be completely closed in order to close an end effector. This is then particularly helpful if an auxiliary element $35_L$ and $35_R$ is guided with the hands and the fingers can therefore not be completely closed.

It can, however, also be necessary for the activation of the gesture control that, additionally, the position $P_{1L}$ or $P_{1R}$ of the controlling hand $30_L$ or $30_R$ is brought into agreement with the position $Q_{1L}$ or $Q_{1R}$ of the controlled end effector 17 or 21 again. The method to align the position can in turn occur analogously to the alignment of the orientation or of the degree of opening. As is shown in FIG. 6, the position of the point $Q_{1R}'$ of the virtual end effector 17' is offset compared to the point $Q_{1R}$ of the end effector 17. The offset can, for example, be displayed by a vector 39. The user can now change the position of his hand until it agrees with the position of the virtual end effector 17''. The agreement can in turn be displayed to the user. After the alignment, the relative position of the hands $30_L$ and $30_R$ as well as the end effectors 17, 21 then agree with each other. In other words, if the fingertips of the left hand $30_L$ and the right hand $30_R$ touch, then the tips of the end effectors 17, 21 should also touch.

In order to design the control of the robot system 11 to be as simple as possible and in particular to enable an intuitive control, the objects 17, 21, 17', 17'' depicted on the screen 29 are preferably depicted such that they follow a hand movement precisely in the direction of the hand movement. If a hand $30_L$, $30_R$ is moved, for example, in the x-direction in the coordinate system $K_G$ of the imaging system, then the controlled object is also moved in the image, such as, for example, the end effector 17 or the virtual end effector 17', in the x-direction in the coordinate system $K_B$ of the screen 29. The same applies for movements having a component in the y-direction or z-direction. The coordinate system $K_B$ of the screen 29 is thereby orientated in the same direction as the coordinate system $K_G$ of the imaging system (the z-axis points, for example, upwards and the x-axis to the right). A hand movement to the right therefore also always results in a movement of the controlled object 17, 17' on the screen to the right, and a movement upwards (in the z-direction) in a corresponding movement of the controlled object 17, 17' on the screen upwards. The actual movement of the object 17, 21 in space differs, however, as a rule, from the movement displayed on the screen 29. In order to achieve such a depiction, there are fundamentally various possibilities.

In the robot system 11 depicted in FIGS. 1 to 6, an individual coordinate system $K_{K1}$, $K_{K2}$ is allocated to each camera 22, 23. During a pivot of the camera 22 or 23, the associated coordinate system $K_{K1}$ or $K_{K2}$ also pivots with the camera. Therefore, the orientation of a camera coordinate system $K_{K1}$ or $K_{K2}$ can be carried out by the corresponding camera 22 or 23 being adjusted. For example, camera 23 can be rotated around its axis 42. Alternatively, the orientation of the camera coordinate system $K_{K1}$ or $K_{K2}$ can be adapted by the user in any manner by means of the control 25 using a coordinate transformation, such that the camera does not necessarily have to be adjusted.

Additionally, the alignment of the camera coordinate systems $K_{K1}$ and $K_{K2}$ should each be identical in relation to the respective cameras 22, 23. The x-axis of the coordinate system $K_{K1}$ of the camera 22 and the x-axis of the coordinate system $K_{K2}$ of the camera 23 introduced into the patient 13 can, for example, each point in the recording direction of the respective camera 22, 23. The orientation of the coordinate system $K_B$ of the screen 29 likewise agrees with the orientation of the coordinate systems $K_{K1}$, $K_{K2}$, wherein the coordinate system $K_B$ is aligned in a fixed manner on the screen 29. For example, the z-axis of $K_B$ always points vertically upwards and the x-axis points into the screen 29 as a normal to the screen surface. If an object recorded by the camera 23, for example, is moved in the z-direction in the coordinate system $K_{K1}$, the object is also moved on the screen 29 in the z-direction in the screen coordinate system $K_B$. The robot system 11 automatically recognises where the end effector 17, 21 is located and controls this accordingly. The relevant coordinate system for the respective end effector 17, 21 is preferably changed automatically if the end effector 17, 21 is guided in and out of the patient 13.

The coordinate system $K_G$ is allocated to the detection region 36. This coordinate system can be aligned according to the coordinate system $K_B$ of the screen 29, but does not have to be. Preferably, however, the y-axis of the coordinate system $K_G$ is aligned substantially in parallel to the y-axis of the coordinate system $K_B$ of the screen 29. The x-axis of the coordinate system $K_G$ is directed substantially frontally to the front in relation to the user.

The real movement of an end effector 17, 21 in space, however, as a rule does not agree with the movement direction displayed on the screen 29 and also does not agree with the movement direction of the controlling hand $30_L$, $30_R$ in space. The end effectors 17, 21 are controlled in particular in the camera coordinate system $K_{K1}$ or $K_{K2}$. Depending on how the camera 22 or 23 is aligned, the camera coordinate system $K_{K1}$ or $K_{K2}$ is also aligned differently in space. In other words, a hand movement in the z-direction of the coordinate system $K_G$ indeed causes a movement of the end effector in the z-direction of the respective camera coordinate system $K_{K1}$ or $K_{K2}$. The actual movement of the end effector in space then, however, depends on the alignment of the z-axis of the camera coordinate system $K_{K1}$ or $K_{K2}$ in space.

The position and alignment (orientation of the x-, y-, z-axes) of the coordinate systems $K_{K1}$, $K_{K2}$ are known to the robot system 11 or to the control unit 25 and can be converted into a global robot coordinate system $K_R$ by a coordinate transformation. As a consequence, all physical parameters in each of the coordinate systems $K_{K1}$, $K_{K2}$, $K_B$, $K_G$ can be converted into corresponding parameters of a different coordinate system by means of coordinate transformation. Therefore, for example, the positions of the points $Q_{1L}$ and $Q_{1R}$ could be described by vectors in the global robot coordinate system $K_R$. The positions of the points $Q_{1L}$ and $Q_{1R}$ of the robot coordinate system $K_R$ could likewise be transformed into the coordinate systems $K_{K1}$ and $K_{K2}$ of the respective camera 22, 23. Therefore, the control 25 can convert the movement parameters of a hand $30_L$, $30_R$, which are detected in the coordinate system $K_G$ into control parameters for an end effector 17, 21 which is operated in the respective camera coordinate system $K_{K1}$ or $K_{K2}$.

The orientation, position and the angle of opening of the end effectors 17, 21 can be determined by the imaging system in an analogous way to the hand $30_L$, $30_R$. The angle of opening can, for example, be set by an angle between the two working elements, as is depicted in FIG. 3. The orientation of the end effectors 17, 21 can be set by the vectors $V_{2L}$ and $V_{2R}$ and the position of the end effectors 17 and 21 can be defined by the position of the limb points $Q_{1L}$ or $Q_{1R}$. If, as has been previously defined, the hand vectors $V_{1L}$ and $V_{1R}$ each run at half of the angle $\alpha_R$ or $\alpha_R$ between the thumb and the index finger, then advantageously it is analogously defined that the end effector vectors $V_{2L}$ or $V_{2R}$ run at half the angle of opening $\phi_L$ or $\phi_R$ between the two working elements of the respective auxiliary element $25_L$ or $25_R$. The individual parameters can be described in any coordinate system $K_{K1}$, $K_{K2}$, $K_R$. In this way, diversely redundant pieces of information can be obtained which can be compared to one another for checking.

The data present in the robot system 11 can be used to recognise the position, the orientation and the angle of opening of an end effector 17, 21. Therefore, for example, the control unit 25 can determine the position of the end effector 17 by means of the position of the robot arm 14. Since the control unit 25 furthermore generates the control commands for the end effectors 17, 21, the orientation and the angle of opening of each end effector 17, 21 are also therefore known to this.

After the activation of the gesture control for one of the end effectors 17, 21, the relevant end effector 17, 21 can be operated by hand. As long as the controlling hand $30_L$, $30_R$ is located in the detection region 36, the control commands executed by the user are converted into corresponding control commands. If, however, the controlling hand $30_L$ or $30_R$ moves from the detection region 36, the gesture control is preferably interrupted. In other words, the end effector 17, 21 is stopped. Therefore, it can be excluded that the end effector 17, 21 executes an action which is not desired. The relevant end effector 17, 21 can be activated again after a new alignment process has been executed.

Figure 7:
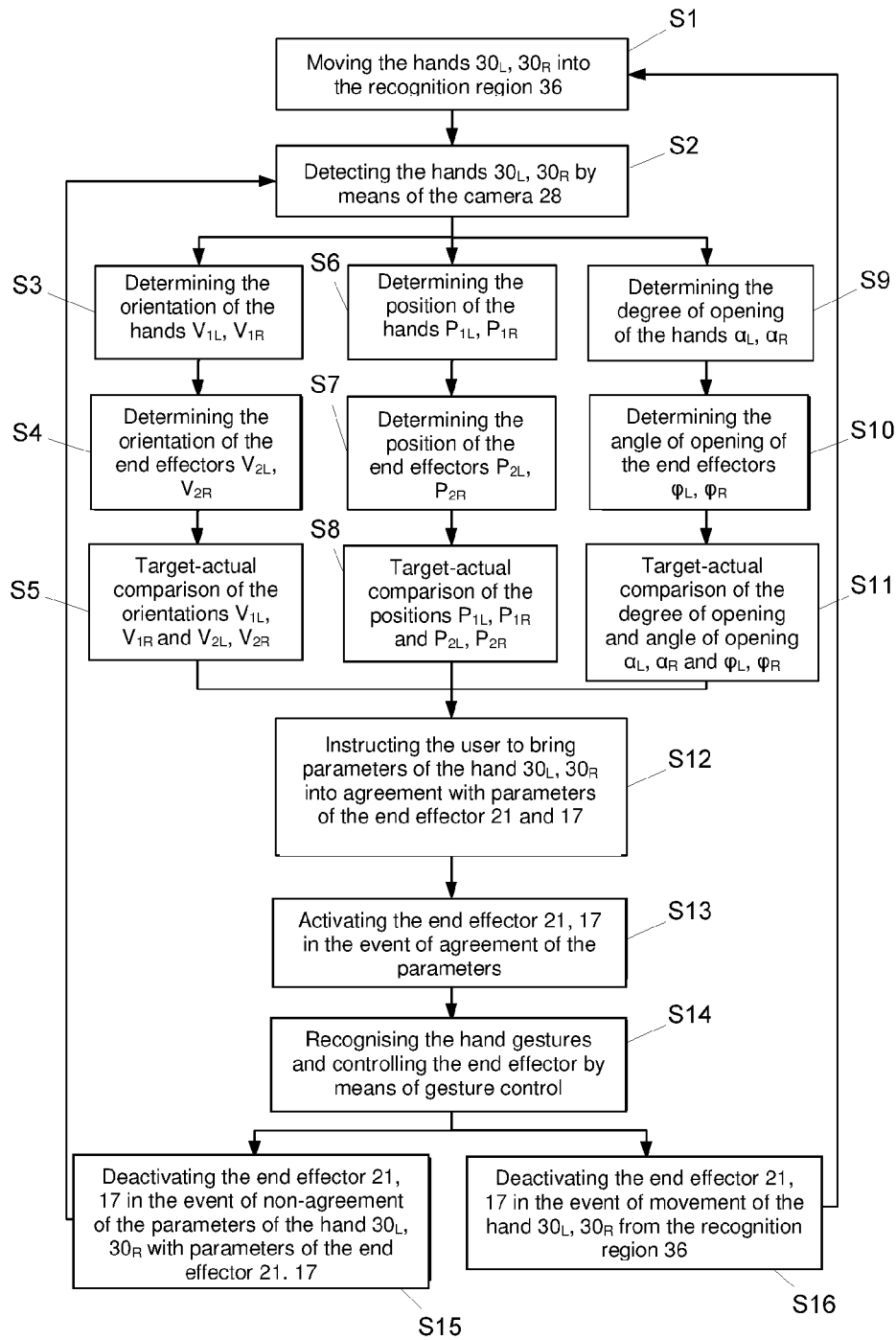
FIG. 7 a schematic depiction of different method steps of a method for controlling a robot system by means of gesture control.

FIG. 7 shows various method steps of a method for controlling the robot system 11 of FIGS. 1 to 6. In step S1, the hands $30_L$, $30_R$ are moved into the detection region 36 and in step S2 are detected by means of the camera 28. In step S3, the determination of the orientation of the hands occurs, wherein the vectors $V_{1L}$, $V_{1R}$ are set. In step S4, the orientation of the end effectors 17, 21 is determined and the vectors $V_{2L}$, $V_{2R}$ are set. In step S5, a target-actual alignment of the orientations then follows.

In step S6, the position of the hands $30_L$ and $30_R$ is determined and corresponding points $P_{1L}$, $P_{1R}$ are set. The determination of the position of the end effectors follows this in step S7, wherein the points $P_{2L}$ and $P_{2R}$ are set. In step S8, finally a target-actual value alignment of the positions follows.

Step S9 describes the determination of the degree of opening of the finger, wherein the angles $\alpha_L$ and $\alpha_R$ are determined. Correspondingly, then in step S10, the angles of opening of the end effectors 17, 21 are determined. In step S11, finally the target-actual value alignment of the degree of opening or angle of opening follows.

In the event of a deviation of the orientations, the positions and/or the degrees of opening, in step 12, an instruction is emitted to the user to implement an alignment. As soon as an agreement of at least one actual value with the respectively associated target value has been achieved, the gesture control is activated. The robot system 11 then recognises the manual control commands executed by the user and controls the end effectors 17, 21 according to the commands.

If a parameter of the hand $30_L$ or $30_R$ no longer agrees with the respective parameter of the end effector 17, 21, the control of this end effector 17, 21 is preferably deactivated (step S15). A deactivation of the end effector 17, 21 preferably also occurs if the controlling hand $30_L$, $30_R$ has moved from the detection region 36.

The end effector 17, 21 can be activated or operated again if the procedure for agreement of the respective parameters is carried out again. If a hand has been moved from the recognition region 36, then it must first be moved into the recognition region 36 again (see step S1). Provided a non-agreement of at least one of the parameters was the trigger of the interruption, while the hands were located in the detection region 36, the renewed determination of the respective parameters can be continued directly (see step S2, S3, S6 and S9).

The steps shown in FIG. 7 can be deposited on a storage medium in the control 25, such that the control 25 can execute it at any time.

The invention claimed is:

1. A control device for controlling a robot system with at least one robot arm on which a surgical instrument is secured which has an end effector, wherein the control device comprising:
    an imaging system which records the control command of at least one hand, evaluates it and converts it into corresponding control commands for one or more components of the robot system, and
    a control unit which is constructed and arranged to:
        determine the orientation and/or the position and/or the degree of opening of the end effector of the surgical instrument as a first parameter or first parameters, and furthermore
        determine the orientation and/or the position and/or the degree of opening of at least one hand as a second parameter or second parameters,
        and in the event that one or more of the first parameters deviate from the respectively corresponding second parameter or in the event that the controlling hand moves out of a detection region, automatically deactivate the gesture control of the end effector, and
        in the event that one or more of the first parameters agree with the respectively corresponding second parameter and in the event that the controlling hand is moved in the detection region, enable a gesture control such that the end effector can be operated by means of the gesture control.

2. The control device according to claim 1, wherein at least two of the second parameters must agree with the respectively corresponding first parameters in order to enable the gesture control.

3. The control device according to claim 1, wherein the control unit is constructed and arranged to emit a signal in the event of a deviation of one more of the first parameters from the respectively corresponding second parameter, said signal being to require the user of the robot system to adapt the orientation and/or position and/or the degree of opening of at least one hand to the corresponding state of the end effector.

4. The control device according to claim 1, wherein in the event of an agreement of one or more of the second parameters with the respectively corresponding first parameter, the control unit is constructed and arranged to emit a signal which signals to the user that an alignment of a hand with the controlled end effector was successful.

5. The control device according to claim 1, wherein the control unit is constructed and arranged to depict a virtual element on a screen, the orientation and/or position and/or degree of opening of which corresponds to that or those of the hand.

6. The control device according to claim 1, wherein the control unit is constructed and arranged to depict a further element on a screen, the orientation and/or position and/or degree of opening of which corresponds to that or those of the controlled end effector, and which serves as a target specification for the alignment between the controlling hand and the controlled end effector.

7. The control device according to claim 1, further comprising a manually operated auxiliary element.

8. The control device according to claim 1, wherein the control unit is constructed and arranged to determine the position of the hand by setting a point on the hand or the associated arm or on an associated auxiliary element and determines this point in a coordinate system of the imaging system.

9. The control device according to claim 1, wherein the control unit is constructed and arranged to determine the orientation of at least one hand by setting at least one vector and determines this in the coordinate system of the imaging system.

10. The control device according to claim 9, wherein to set the vector, the control unit is constructed and arranged to set at least one further point on the hand and/or on an auxiliary element.

11. The control device according to claim 10, wherein the vector lies on a plane which is spanned by at least three of the set points.

12. The control device according to claim 1, wherein the control unit is constructed and arranged to set at least one point on the hand and/or on the auxiliary element which lies on a tip of a finger or of the auxiliary element.

13. The control device according to claim 1, wherein the control unit is constructed and arranged to determine the degree of opening of at least one hand by setting two lines, and determines the angle between the lines in the coordinate system of the imaging system.

14. The control device according to claim 11, wherein the control unit is constructed and arranged to determine the degree of opening of at least one hand by determining the distance between two points on the hand.

15. The control device according to claim 7, wherein the manually operated auxiliary element comprises an inertial sensor which can measure a position of the auxiliary element in space and/or a movement of the auxiliary element in or around three spatial axes.

16. The control device according to claim 1, wherein the control unit is constructed and arranged such that a control movement of a hand is converted into a corresponding movement of the end effector using a predetermined scaling factor.

17. The control device according to claim 1, wherein it comprises a screen on which an object controlled by means of gesture control is depicted, wherein the orientation of at most only two axes of a coordinate system of the imaging system agrees with the orientation of the corresponding axes of a coordinate system of the screen and the object is displayed such that it is moved on the screen in relation to the coordinate system of the screen in the same direction as the movement of the hand in relation to the coordinate system of the imaging system.

18. The control device according to claim 1, wherein a camera is provided which records the end effector, and a coordinate system of the camera is aligned to the image axes of the image recorded by the camera, wherein one of the axes of the coordinate system of the camera points in the viewing direction of the camera.

19. The control device according to claim 18, wherein the control unit is constructed and arranged such that a control command of a hand in the coordinate system of the imaging system is converted into a corresponding movement of the end effector in the coordinate system of the camera.

20. The control device according to claim 19, wherein to control the end effector, the active coordinate system switches between the coordinate systems of the camera, depending on by which camera the end effector is recorded.

21. A method for controlling a robot system by means of at least one hand, comprising the following steps:
  determining an orientation and/or a position and/or a degree of opening of an end effector of a surgical instrument as a first parameter or first parameters;
  determining the orientation and/or the position and/or the degree of opening of at the least one hand ($30_L$, $30_R$) as a second parameter or second parameters;
  comparing at least one first parameter with the respectively corresponding second parameter;
  in the event that one or more of the first parameters deviate from the respectively corresponding second parameter or in the event that the controlling hand moves out of a detection region, automatically deactivating the gesture control of the end effector; and
  in the event that one or more of the first parameters agree with the respectively corresponding second parameter and in the event that the controlling hand is moved in the detection region, enabling the gesture control such that the end effector can be controlled using the at least one hand.

* * * * *